United States Patent [19]

Sawa et al.

[11] Patent Number: 4,567,259

[45] Date of Patent: Jan. 28, 1986

[54] ISOCYANURIC ACID ADDUCT OF 2-VINYL-4,6-DIAMINO-S-TRIAZINE

[75] Inventors: Natsuo Sawa, Nakatado; Takeshi Masuda, Marugame; Takashi Mizui, Kawagoe, all of Japan

[73] Assignee: Shikoku Chemicals Corp., Kagawa, Japan

[21] Appl. No.: 694,958

[22] Filed: Jan. 25, 1985

[30] Foreign Application Priority Data

Jan. 26, 1984 [JP] Japan .................................. 59-13121

[51] Int. Cl.⁴ ........................................... C07D 403/12
[52] U.S. Cl. .................................................. 544/207
[58] Field of Search ......................................... 544/207

[56] References Cited

U.S. PATENT DOCUMENTS 4,189,577  2/1980  Sawa et al. ......................... 544/222

Primary Examiner—John M. Ford

Attorney, Agent, or Firm—Sherman & Shalloway

[57] ABSTRACT

Disclosed is an isocyanuric acid adduct of 2-vinyl-4,6-diamino-S-triazine represented by the following structural formula:

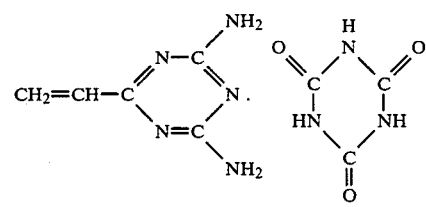

This adduct is prepared by heating 2-vinyl-4,6-diamino-S-triazine and isocyanuric acid in the presence of water, preferably by using sodium sulfide as a polymerization inhibitor. This adduct is valuable as a hardening agent for an epoxy resin.

4 Claims, No Drawings

ISOCYANURIC ACID ADDUCT OF 2-VINYL-4,6-DIAMINO-S-TRIAZINE

BACKGROUND OF THE INVENTION (1) Field of the Invention

The present invention relates to an isocyanuric acid adduct of 2-vinyl-4,6-diamino-S-triazine and a process for the synthesis of said adduct. Moreover, the present invention relates to a process for hardening an epoxy resin with this novel adduct as a curing agent.

(2) Description of the Prior Art

It is known that isocyanuric acid forms an adduct or intermolecular compound with a certain amine compound. For example, in the specification of U.S. Pat. No. 4,189,577 to Sawa et al., it is taught that isocyanuric acid forms a stable adduct with a specific imidazole derivative.

SUMMARY OF THE INVENTION

We made research with a view to developing a novel curing agent for an epoxy resin. As a result, we succeeded in synthesizing a novel adduct from 2-vinyl-4,6-diamino-S-triazine and isocyanuric acid. We found that when this novel adduct is incorporated as a curing agent into an epoxy resin, the pot life, that is, the storage stability, of the resulting epoxy resin composition is improved and the novel adduct exerts an excellent curing function when the composition is heated.

In accordance with a fundamental aspect of the present invention, there is proviced an isocyanuric acid adduct of 2-vinyl-4,6-diamino-S-triazine represented by the following structural formula:

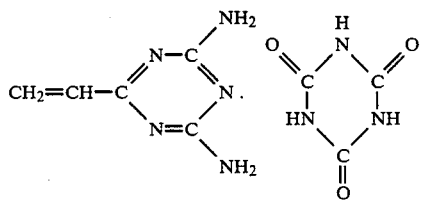

In accordance with another aspect of the present invention, there is provided a process for the preparation of an isocyanuric acid adduct of 2-vinyl-4,6-diamino-S-triazine, which comprises heating 2-vinyl-4,6-diamino-S-triazine represented by the following structural formula:

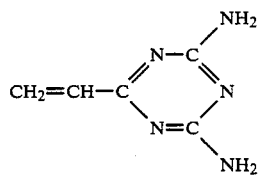

and isocyanuric acid represented by the following structural formula:

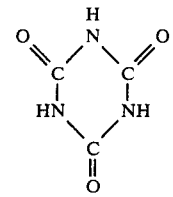

in the presence of water.

In accordance with still another aspect of the present invention, there is provided a curing agent, which comprises an isocyanuric acid adduct of 2-vinyl-4,6-diamino-S-triazine represented by the above structural formula (1), for a polyepoxide resin.

DETAILED DESCRIPTION OF THE INVENTION

The adduct of the present invention is a compound formed by reacting substantially equimolar amounts of 2-vinyl-4,6-diamino-S-triazine and isocyanuric acid. As described in detail hereinafter, this adduct is stable in water, and the adduct is decomposed by an acid or alkali or by heating and shows a polymerizing property.

Several processes are known for the synthesis of 2-vinyl-4,6-diamino-S-triazine (hereinafter referred to as "VT"), which is used as the starting substance in the present invention. For example, there can be mentioned a process comprising reacting biguanide with acrylic acid chloride (C. G. Overbverger et al.; J.A.C.S., 80, 988 (1958)), a process comprising reacting dicyandiamide with $\beta$-dimethylaminopropionitrile (French Pat. No. 1,563,255 (1967) to Hoechst AG), a process comprising heating 1,2-di(4',6'-diamino-S-triazinyl(2'))-cyclobutane at 320° C. under a reduced pressure (Japanese Patent Publication No. 35068/71 to Asahi Kasei) and a process comprising heating 2-$\beta$-methoxyethyl-4,6-diamino-S-triazine at 350° C. in a nitrogen current (Ger. Offen. No. 2,135,881 (1973) to Suddeutsche Kalkstickstoff Werke AG).

Properties of VT prepared according to the processes described above are as shown below.

Melting Point: 239°–241° C. (W).

Solubility: Easily soluble in acetic acid, soluble in hot water, hardly soluble in hot methanol, hot ethanol and hot acetone, and substantially neutral.

Infrared Absorption Spectrum $\nu_{cm^{-1}}^{KBr}$: 3340, 3170, 1680 (fourth absorption), 1655 (second absorption), 1550 (first absorption), 1460 (fifth absorption), 1425 (third absorption, 1370, 1265, 1130, 980, 960, 835 (sixth absorption).

Nuclear Magnetic Resonance ($d_6$-DMSO), $\delta$: 6.76 (multiplet, 4H), 6.35–6.45 (triplet, 2H), 5.59–5.72 (quadruplet, 1H).

Elementary Analysis Values: C=44.28%, H=5.07%, N=50.02%.

We found that when isocyanuric acid (hereinafter referred to as "ICA"), which is now prepared in a large quantities on an industrial scale by thermal decomposition of urea, is heated with VT in the presence of water, an ICA adduct of VT is formed according to the following reaction equation:

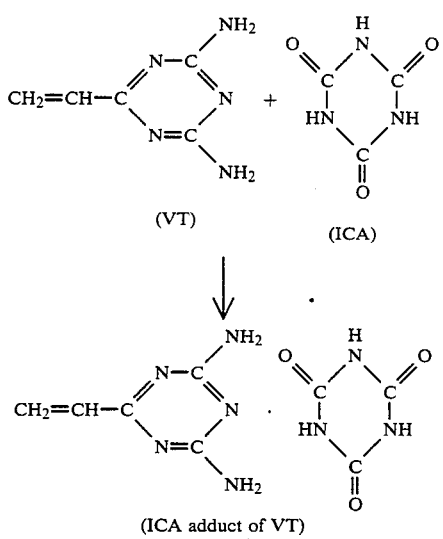

(VT)   (ICA)

↓

(ICA adduct of VT)

An embodiment of the above reaction will now be described.

An appropriate amount of sodium sulfide ($Na_2S.9H_2O$) as a polymerization inhibitor is added to equimolar amounts of VT and ICA, and water is added in such an amount that the reactants are completely dissolved in water when heated. The mixture is heated with to dissolve the reactants completely in water, and the solution was cooled and a precipitated crude product is collected by filtration. Some other polymerization inhibitors (such as hydroquinone) can be used sintead of sodium sulfide, though sodium sulfide is most preferred from the economical viewpoint. Since the infrared absorption spectrum and thin layer chromatogram of the obtained crude product are in agreement with those of the pure product, it is considered that the purity of the crude product obtained according to the above method is considerably high.

It is preferred that the amount of added sodium sulfide is between 0.001 and 0.1 mole, especially 0.005 and 0.05 mole per mole of VT, and that the amount of water is between 100 and 3 times, especially between 30 and 10 times, of that of the adduct. The heating temperature is not particularly critical, so far as the reaction between VT and ICA is completed. However, it is preferred that the heating temperature is between 50° to 100° C., especially 60° to 90° C.

The crude product may be recrystallized from water to purify the product. In the recrystallization, a small amount of sodium sulfide is preferably added to water in advance so as to prevent polymerization. The so-obtained ICA adduct of VT is a novel substance. This adduct is in the form of a colorless crystal and is slightly acidic.

Melting Point: 250° C. or higher.

Solubility: Soluble in hot water, easily soluble in acetic acid and DMSO, insoluble in acetone, methanol or ethanol, and polymerizable.

Reactivity: The adduct reacts with an aqueous solution of potassium carbonate at room temperature to give VT, and on the other hand the adduct reacts with dilute hdyrochloric acid at room temperature to give a crystal of ICA.

Thin layer Chromatography (silica G, EtOH, coloration with $I_2$: Rf=0.0

Infrared Absorption Spectrum $\nu_{cm^{-1}}^{KBr}$: 1770 (fourth absorption), 1710 (first absoprtion), 1635 (fifth absorption), 1530 (second absorption), 1425 (third abosrption), 750 (sixth absorption).

Nuclear Magnetic Resoancne ($d_6$-DMSO), δ: 5.61 (two doublets, 2H) (vinyl group), 6.70 (multipelt, 4H) (amino group).

Mass Spectrum, m/e: 137 (VT), 129 (CIA), 111 (VT, vinyl group +H), 43 (—CONH—).

The novel adduct of the present invention can be used in various fields by utilizing the above-mentioned properties, for example, as a hardening agent for an epoxy resin, especially a one-pack type epoxy resin compositon.

Various hardening agents or curing agents are known for epoxy resins, that is, polyepoxy compounds. However, a few of them are satisfactory in the combination of the storage storability, that is, the pot life, of a curing agent-incorporated epoxy resin composition and the heat-curing property. By dint of the above-mentioned characteristic properties, the novel adduct of the present invention provides a one-pack type epoxy resin composition having a prolonged pot life and exhibits an excellent curing property under heating.

The novel curing agent according to the present invention is used in an amount of 1 to 30 parts by weight, especially 3 to 20 parts by weight, per 100 parts by weight of an epoxy resin having more than one epoxy group, i.e., more than one oxirane ring, in one molecule, namely a polyepoxy compound.

In the epoxy resin composition according to the present invention, the polyepoxy compound contains more than one epoxy group on the average in one molecule. The epoxy group may be in the form of either

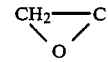

located on the molecule end or

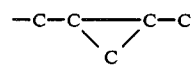

located in the interior of the molecule. The polyepoxy compound may be any of aliphatic, alicyclic, aromatic and heterocyclic polyepoxy compounds. Further, it may be substituted by non-inhibitory groups such as hydroxyl, alkyl, alkoxy, ester, acetal and ether groups.

Most preferred polyepoxy compounds include polyglycidyl ethers of polyhydric phenols such as bisphenol A, bisphenol F, resorcinol, hydroquinone, 4,4-diphenol, dihydroxydiphenylsulfone, phenol-formaldehyde resins and cresol-formaldehyde resins.

Other suitable polyepoxy compounds include glycidyl ethers and glycidyl esters of polyhydric alcohols such as ethylene glycol, propylene glycol, glycerin, trimethylol propane and 1,4-butane diol, polyglycidyl esters of polycarboxylic acids such as phthalic acid, tetrahydrophthalic acid, hexahydrophthalic acid, methylenedomethylenetetrahydrophthalic acid, adipic acid and dimer acid, glycidyl amines derived from polyamines such as aniline and 4,4'-diaminodiphenylmethane, epoxidized polyolefins such as vinylchlorohexene dioxide, 3,4-epoxycyclohexylmethyl-3,4-epoxycyclohexane-carboxylate and bis-(3,4-epoxy-6-methylcyclohexylmethyl)-adipate, and epoxidized vegetable oils.

An epoxy resin marketed under the tradename of "Epikote 828" is especially preferred.

The epoxy resin composition according to the present invention may further comprise, if desired, a pigment, a plasticizer, a filler, a reactive diluent composed of a monoepoxy compound such as butyl glycidyl ether, phenyl glycidyl ether or styrene oxide, a solvent and the like according to know recipes.

A curing agent composed of the novel adduct of the present invention for epoxy resins may be used singly or in combination with a known curing agent for epoxy resins.

The present invention will now be described in detail with reference to the following examples that by no means limit the scope of the invention.

EXAMPLE 1

A stainless steel reaction vessel having a capacity of 20 l was charged with 1 mole (137 g) of VT, 5 l of water and 0.01 mole (2.4 g) of Na$_2$S.9H$_2$O, and the charge was heated with stirring so that the inner temperature was about 80° C. At this point, the reaction mixture was heterogeneous. Then, 1 mole (129 g) of ICA was added at a time, and when the mixture was heated with stirring for a while, the mixture became homogeneous. The homogeneous solution was cooled and the precipitated crystal was collected by filtration to give 0.95 mole (252.7 g) of a crude product (the yield was 95 mole%). The crude product was characterized by a melting point higher than 250° C., an Rf value of 0.0 in the thin layer chromatography (silica G, EtOH, coloration with I$_2$) and the same infrared absorpiton spectrum as that of a refined product described below.

0.95 mole (252 g) of the above-mentioned crude product was recrystallized from 18 l of water containing 2.4 g of Na$_2$S.9H$_2$O, to give 0.88 mole (235 g) of a refined product (the yield was 88.3 mole%).

EXAMPLE 2

Into 100 parts by weight of solid Epikote 828 (diglycidyl ether of bisphenol A supplied by Yuka Shell K.K.) was incorporated 10 parts by weight of the ICA adduct of VT obtained in Example 1, and 0.2 g of the mixture was sealed in an aluminum cell and subjected to the differential thermal analysis at a temperature-elevating rate of 5° C./min. A peak attributed to heat generation by curing was observed at 163° C.

EXAMPLE 3

Into 100 parts by weight of Epikote YX (epoxy resin comprising Epikote 828 and a plastic elastomer, supplied by Yuka Shell epoxy K.K.) was incorporated 10 parts of the ICA adduct of VT obtained in Example 1, and the composition was sufficiently pulverized and kneaded by a three-roll mill and 50 parts by weight of calcium carbonate was added to the mixture. The mixture was sufficiently stirred and blended to obtain a one-pack type composition.

The viscosity of the composition was 760 P as measured at 25° C., and the gel time at 150° C. was 3 minutes and 6 seconds as determined according to the hot plate method.

When the composition was stored at 40° C., the number of days required for reaching 2 times higher viscosity than the initial viscosity was 14. This indicates that the composition had a very good storage stability.

The glass transition point of a cured product obtained by heating and curing the composition at 100° C. for 4 hours and at 200° C. for 4 hours was 165° C., and the flexural strength of the cured product was 8.5 kg/mm$^2$ as measured at 25° C.

We claim:

1. An isocyanuric acid adduct of 2-vinyl-4,6-diamino-S-triazine represented by the following structural formula:

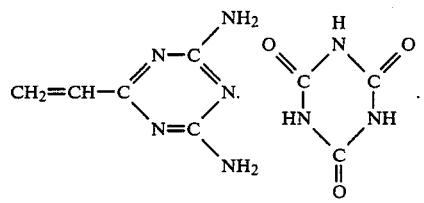

2. A process for the preparation of an isocyanuric acid adduct of 2-vinyl-4,6-diamino-S-triazine, which comprises heating 2-vinyl-4,6-diamino-S-triazine represented by the following structural formula:

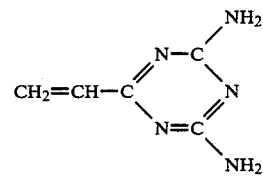

and isocyanuric acid represented by the following structural formula:

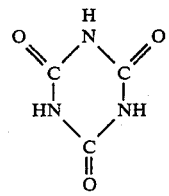

in the presence of water.

3. A process according to claim 2, wherein heating is carried out so that the temperature of the reaction mixture is between 50° and 100° C.

4. A process according to claim 2, wherein heating is carried out in the presence of sodium sulfide as a polymerization inhibitor.

* * * * *